(12) United States Patent
Drews et al.

(10) Patent No.: US 8,603,161 B2
(45) Date of Patent: *Dec. 10, 2013

(54) ATTACHMENT DEVICE AND METHODS OF USING THE SAME

(75) Inventors: Michael J. Drews, Palo Alto, CA (US);
Donnell W. Gurskis, Belmont, CA (US);
Steven R. Bacich, Half Moon Bay, CA (US)

(73) Assignee: Medtronic, Inc., Fridley, MN (US)

( * ) Notice: Subject to any disclaimer, the term of this patent is extended or adjusted under 35 U.S.C. 154(b) by 1189 days.

This patent is subject to a terminal disclaimer.

(21) Appl. No.: 12/498,195

(22) Filed: Jul. 6, 2009

(65) Prior Publication Data

US 2010/0010616 A1 Jan. 14, 2010

Related U.S. Application Data

(63) Continuation of application No. 10/681,700, filed on Oct. 8, 2003, now Pat. No. 7,556,647.

(51) Int. Cl.
*A61B 17/10* (2006.01)
(52) U.S. Cl.
USPC ........... 623/2.11; 606/142; 606/215; 606/216
(58) Field of Classification Search
USPC ......... 606/139, 142, 148, 151, 215, 216, 219; 623/904, 2.11
See application file for complete search history.

(56) References Cited

U.S. PATENT DOCUMENTS

| | | | |
|---|---|---|---|
| 3,143,742 A | 8/1964 | Cromie | |
| 3,320,974 A | 5/1967 | High et al. | |
| 3,370,305 A | 2/1968 | Goott et al. | |
| 3,371,352 A | 3/1968 | Siposs | |
| 3,409,013 A | 11/1968 | Berry | |
| 3,464,065 A | 9/1969 | Cromie | |
| 3,546,710 A | 12/1970 | Ivanovich et al. | |

(Continued)

FOREIGN PATENT DOCUMENTS

| | | |
|---|---|---|
| CN | 2356656 | 1/2000 |
| DE | 19532973 | 11/1996 |

(Continued)

OTHER PUBLICATIONS

Lutter, et al., Percutaneous Valve Replacement: Current State and Future Prospects; Ann. Thorac. Surg. 2004;78:2199-2206.

(Continued)

*Primary Examiner* — Melanie Tyson
*Assistant Examiner* — Todd J Scherbel

(57) ABSTRACT

Devices for attaching a first mass and a second mass and methods of making and using the same are disclosed. The devices can be made from an resilient, elastic or deformable materials. The devices can be used to attach a heart valve ring to a biological annulus. The devices can also be used for wound closure or a variety of other procedures such as anchoring a prosthesis to surrounding tissue or another prosthesis, tissue repair, such as in the closure of congenital defects such as septal heart defects, tissue or vessel anastomosis, fixation of tissue with or without a reinforcing mesh for hernia repair, orthopedic anchoring such as in bone fusing or tendon or muscle repair, ophthalmic indications, laparoscopic or endoscopic tissue repair or placement of prostheses, or use by robotic devices for procedures such as those above performed remotely.

13 Claims, 13 Drawing Sheets

(56) References Cited

U.S. PATENT DOCUMENTS

| | | |
|---|---|---|
| 3,571,815 A | 3/1971 | Somyk |
| 3,574,865 A | 4/1971 | Hamaker |
| 3,628,535 A | 12/1971 | Ostrowsky et al. |
| 3,686,740 A | 8/1972 | Shiley |
| 3,691,567 A | 9/1972 | Cromie |
| 3,710,744 A | 1/1973 | Goodenough et al. |
| 3,744,060 A | 7/1973 | Bellhouse et al. |
| 3,755,823 A | 9/1973 | Hancock |
| 3,800,403 A | 4/1974 | Anderson |
| 3,839,741 A | 10/1974 | Haller |
| 3,959,827 A | 6/1976 | Kaster |
| 3,974,854 A | 8/1976 | Kurpanek |
| 3,996,623 A | 12/1976 | Kaster |
| 3,997,923 A | 12/1976 | Possis |
| 4,035,849 A | 7/1977 | Angell et al. |
| 4,078,268 A | 3/1978 | Possis |
| 4,078,468 A | 3/1978 | Civitello |
| 4,084,268 A | 4/1978 | Ionexcu et al. |
| 4,106,129 A | 8/1978 | Carpentier et al. |
| 4,164,046 A | 8/1979 | Cooley |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,245,358 A | 1/1981 | Moasser |
| 4,259,753 A | 4/1981 | Liotta et al. |
| 4,291,420 A | 9/1981 | Reul |
| 4,297,749 A | 11/1981 | Davis et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,477,930 A | 10/1984 | Totten et al. |
| 4,485,816 A | 12/1984 | Krumme |
| 4,501,030 A | 2/1985 | Lane |
| 4,506,394 A | 3/1985 | Bedard |
| 4,535,483 A | 8/1985 | Klawitter et al. |
| 4,548,202 A | 10/1985 | Duncan |
| 4,605,407 A | 8/1986 | Black et al. |
| 4,626,255 A | 12/1986 | Reichart et al. |
| 4,629,459 A | 12/1986 | Ionescu et al. |
| 4,665,906 A | 5/1987 | Jervis |
| 4,666,442 A | 5/1987 | Arru et al. |
| 4,680,031 A | 7/1987 | Alonso |
| 4,683,883 A | 8/1987 | Martin |
| 4,687,483 A | 8/1987 | Fisher et al. |
| 4,692,164 A | 9/1987 | Dzemeshkevich et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,743,253 A | 5/1988 | Magladry |
| 4,758,151 A | 7/1988 | Arru et al. |
| 4,775,378 A | 10/1988 | Knoch et al. |
| 4,778,461 A | 10/1988 | Pietsch et al. |
| 4,790,843 A | 12/1988 | Carpentier et al. |
| 4,816,029 A | 3/1989 | Penny, III et al. |
| 4,851,000 A | 7/1989 | Gupta |
| 4,865,600 A | 9/1989 | Carpentier et al. |
| 4,888,009 A | 12/1989 | Lederman et al. |
| 4,892,541 A | 1/1990 | Alonso |
| 4,917,097 A | 4/1990 | Proudian et al. |
| 4,917,698 A | 4/1990 | Carpentier et al. |
| 4,935,030 A | 6/1990 | Alonso |
| 4,960,424 A | 10/1990 | Grooters |
| 4,993,428 A | 2/1991 | Arms |
| 4,994,077 A | 2/1991 | Dobben |
| 5,002,567 A | 3/1991 | Bona et al. |
| 5,010,892 A | 4/1991 | Colvin et al. |
| 5,032,128 A | 7/1991 | Alonso |
| 5,035,709 A | 7/1991 | Wieting et al. |
| 5,037,434 A | 8/1991 | Lane |
| 5,071,431 A | 12/1991 | Sauter et al. |
| 5,104,406 A | 4/1992 | Curcio et al. |
| 5,147,391 A | 9/1992 | Lane |
| 5,163,953 A | 11/1992 | Vince |
| 5,163,954 A | 11/1992 | Curcio et al. |
| 5,163,955 A | 11/1992 | Love et al. |
| 5,178,633 A | 1/1993 | Peters |
| 5,192,303 A | 3/1993 | Gatturna |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,346 A | 3/1995 | Walker et al. |
| 5,397,348 A | 3/1995 | Campbell et al. |
| 5,397,351 A | 3/1995 | Pavcnik et al. |
| 5,406,857 A | 4/1995 | Eberhardt et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,531,784 A | 7/1996 | Love et al. |
| 5,533,515 A | 7/1996 | Coller et al. |
| 5,549,665 A | 8/1996 | Vesely et al. |
| 5,549,666 A | 8/1996 | Hata et al. |
| 5,562,729 A | 10/1996 | Purdy et al. |
| 5,571,175 A | 11/1996 | Vanney |
| 5,571,215 A | 11/1996 | Sterman et al. |
| 5,573,007 A | 11/1996 | Bobo, Sr. |
| 5,573,543 A | 11/1996 | Akopov et al. |
| 5,578,076 A | 11/1996 | Krueger et al. |
| 5,584,803 A | 12/1996 | Stevens et al. |
| 5,607,470 A | 3/1997 | Milo |
| 5,613,982 A | 3/1997 | Goldstein |
| 5,618,307 A | 4/1997 | Donlon et al. |
| 5,626,607 A | 5/1997 | Malecki et al. |
| 5,628,789 A | 5/1997 | Vanney et al. |
| 5,662,704 A | 9/1997 | Gross |
| 5,669,917 A | 9/1997 | Sauer |
| 5,693,090 A | 12/1997 | Unsworth et al. |
| 5,695,503 A | 12/1997 | Krueger et al. |
| 5,713,952 A | 2/1998 | Vanney et al. |
| 5,713,953 A | 2/1998 | Vallana et al. |
| 5,716,370 A | 2/1998 | Williamson, IV et al. |
| 5,716,399 A | 2/1998 | Love |
| 5,720,755 A | 2/1998 | Dakov |
| 5,725,554 A | 3/1998 | Simon |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,807,405 A | 9/1998 | Vanney et al. |
| 5,814,097 A | 9/1998 | Sterman et al. |
| 5,814,098 A | 9/1998 | Hinnenkamp et al. |
| 5,814,100 A | 9/1998 | Carpentier et al. |
| 5,824,060 A | 10/1998 | Christie et al. |
| 5,824,061 A | 10/1998 | Quijano et al. |
| 5,824,064 A | 10/1998 | Taheri |
| 5,830,239 A | 11/1998 | Toomes |
| 5,840,081 A | 11/1998 | Andersen et al. |
| 5,843,179 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |

(56) References Cited

U.S. PATENT DOCUMENTS

| | | |
|---|---|---|
| 5,855,603 A | 1/1999 | Reif |
| 5,860,992 A | 1/1999 | Daniel |
| 5,861,028 A | 1/1999 | Angell |
| 5,865,801 A | 2/1999 | Houser |
| 5,876,436 A | 3/1999 | Vanney et al. |
| 5,879,371 A | 3/1999 | Gardiner et al. |
| 5,891,160 A | 4/1999 | Williamson, IV et al. |
| 5,891,195 A | 4/1999 | Klostermeyer et al. |
| 5,895,420 A | 4/1999 | Mirsch, II et al. |
| 5,902,308 A | 5/1999 | Murphy |
| 5,908,450 A | 6/1999 | Gross et al. |
| 5,908,452 A | 6/1999 | Bokros et al. |
| 5,910,170 A | 6/1999 | Reimink et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,969 A | 8/1999 | Carpentier et al. |
| 5,935,163 A | 8/1999 | Gabbay |
| 5,957,949 A | 9/1999 | Leonhardt et al. |
| 5,961,549 A | 10/1999 | Nguyen et al. |
| 5,961,550 A | 10/1999 | Carpentier et al. |
| 5,972,004 A | 10/1999 | Williamson, IV et al. |
| 5,972,024 A | 10/1999 | Northrup, III et al. |
| 5,976,183 A | 11/1999 | Ritz |
| 5,984,949 A | 11/1999 | Levin |
| 5,984,959 A | 11/1999 | Robertson et al. |
| 5,984,973 A | 11/1999 | Girard et al. |
| 6,007,577 A | 12/1999 | Vanney et al. |
| 6,010,531 A | 1/2000 | Donlon et al. |
| 6,042,607 A | 3/2000 | Williamson, IV et al. |
| 6,045,576 A | 4/2000 | Starr et al. |
| 6,059,827 A | 5/2000 | Fenton, Jr. |
| 6,066,160 A | 5/2000 | Colvin et al. |
| 6,068,657 A | 5/2000 | Lapeyre et al. |
| 6,074,041 A | 6/2000 | Imanaka et al. |
| 6,074,417 A | 6/2000 | Peredo |
| 6,074,418 A | 6/2000 | Buchanan et al. |
| 6,081,737 A | 6/2000 | Shah |
| 6,083,179 A | 7/2000 | Oredsson |
| 6,096,074 A | 8/2000 | Pedros |
| 6,099,475 A | 8/2000 | Seward et al. |
| 6,102,944 A | 8/2000 | Huynh |
| 6,106,550 A | 8/2000 | Magovern et al. |
| 6,110,200 A | 8/2000 | Hinnenkamp |
| 6,113,632 A | 9/2000 | Reif |
| 6,117,091 A | 9/2000 | Young et al. |
| 6,126,007 A | 10/2000 | Kari et al. |
| 6,129,758 A | 10/2000 | Love |
| 6,139,575 A | 10/2000 | Shu et al. |
| 6,143,024 A | 11/2000 | Campbell et al. |
| 6,143,025 A | 11/2000 | Stobie et al. |
| 6,149,658 A | 11/2000 | Gardiner et al. |
| 6,162,233 A | 12/2000 | Williamson, IV et al. |
| 6,165,183 A | 12/2000 | Kuehn et al. |
| 6,168,614 B1 | 1/2001 | Anderson et al. |
| 6,176,877 B1 | 1/2001 | Buchanan et al. |
| 6,183,512 B1 | 2/2001 | Howanec, Jr. et al. |
| 6,197,042 B1 * | 3/2001 | Ginn et al. .............. 606/213 |
| 6,197,054 B1 | 3/2001 | Hamblin, Jr. et al. |
| 6,200,306 B1 | 3/2001 | Klostermeyer |
| 6,203,553 B1 | 3/2001 | Robertson |
| 6,214,043 B1 | 4/2001 | Krueger et al. |
| 6,217,610 B1 | 4/2001 | Carpentier et al. |
| 6,217,611 B1 | 4/2001 | Klostermeyer |
| 6,231,561 B1 | 5/2001 | Frazier et al. |
| 6,231,602 B1 | 5/2001 | Carpentier et al. |
| 6,241,765 B1 | 6/2001 | Griffin et al. |
| 6,245,102 B1 | 6/2001 | Jayaraman |
| 6,245,105 B1 | 6/2001 | Nguyen et al. |
| 6,254,636 B1 | 7/2001 | Peredo |
| 6,264,691 B1 | 7/2001 | Gabbay |
| 6,270,526 B1 | 8/2001 | Cox |
| 6,270,527 B1 | 8/2001 | Campbell et al. |
| 6,283,127 B1 | 9/2001 | Sterman et al. |
| 6,283,995 B1 | 9/2001 | Moe et al. |
| 6,287,339 B1 | 9/2001 | Vazquez et al. |
| 6,290,674 B1 | 9/2001 | Roue et al. |
| 6,299,638 B1 | 10/2001 | Sauter |
| 6,309,417 B1 | 10/2001 | Spence |
| 6,312,447 B1 | 11/2001 | Grimes |
| 6,312,465 B1 | 11/2001 | Griffin et al. |
| 6,319,280 B1 | 11/2001 | Schoon |
| 6,319,281 B1 | 11/2001 | Patel |
| 6,322,588 B1 | 11/2001 | Ogle et al. |
| 6,328,727 B1 | 12/2001 | Frazier et al. |
| 6,328,763 B1 | 12/2001 | Love et al. |
| 6,338,740 B1 | 1/2002 | Carpentier |
| 6,350,281 B1 | 2/2002 | Rhee |
| 6,358,278 B1 | 3/2002 | Brendzel et al. |
| 6,358,556 B1 | 3/2002 | Ding et al. |
| 6,371,983 B1 | 4/2002 | Lane |
| 6,391,053 B1 | 5/2002 | Brendzel et al. |
| 6,395,025 B1 | 5/2002 | Fordenbacher et al. |
| 6,402,780 B2 | 6/2002 | Williamson, IV et al. |
| 6,409,759 B1 | 6/2002 | Peredo |
| 6,413,275 B1 | 7/2002 | Nguyen et al. |
| 6,419,696 B1 | 7/2002 | Ortiz et al. |
| 6,425,902 B1 | 7/2002 | Love |
| 6,425,916 B1 | 7/2002 | Garrison et al. |
| 6,440,164 B1 | 8/2002 | DiMatteo et al. |
| 6,447,524 B1 | 9/2002 | Knodel |
| 6,454,799 B1 | 9/2002 | Schreck |
| 6,458,153 B1 | 10/2002 | Bailey et al. |
| 6,461,382 B1 | 10/2002 | Cao |
| 6,468,305 B1 | 10/2002 | Otte |
| 6,503,272 B2 | 1/2003 | Duerig et al. |
| 6,514,265 B2 | 2/2003 | Ho et al. |
| 6,530,952 B2 | 3/2003 | Vesely |
| 6,547,827 B2 | 4/2003 | Carpentier et al. |
| 6,551,332 B1 | 4/2003 | Nguyen et al. |
| 6,558,418 B2 | 5/2003 | Carpentier et al. |
| 6,569,196 B1 | 5/2003 | Vesely |
| 6,582,462 B1 | 6/2003 | Andersen et al. |
| 6,585,766 B1 | 7/2003 | Huynh et al. |
| 6,589,279 B1 | 7/2003 | Anderson et al. |
| 6,598,307 B2 | 7/2003 | Love et al. |
| 6,602,289 B1 | 8/2003 | Colvin et al. |
| 6,607,541 B1 | 8/2003 | Gardiner et al. |
| 6,613,059 B2 | 9/2003 | Ho et al. |
| 6,613,085 B1 | 9/2003 | Anderson et al. |
| 6,641,593 B1 | 11/2003 | Schaller et al. |
| 6,652,578 B2 | 11/2003 | Bailey et al. |
| 6,676,671 B2 | 1/2004 | Robertson et al. |
| 6,678,962 B1 | 1/2004 | Love et al. |
| 6,682,559 B2 | 1/2004 | Myers et al. |
| 6,685,739 B2 | 2/2004 | DiMatteo et al. |
| 6,692,513 B2 | 2/2004 | Streeter et al. |
| 6,695,859 B1 | 2/2004 | Golden et al. |
| 6,709,457 B1 | 3/2004 | Otte et al. |
| 6,716,243 B1 | 4/2004 | Colvin et al. |
| 6,716,244 B2 | 4/2004 | Klaco |
| 6,716,789 B1 | 4/2004 | Heineke et al. |
| 6,719,790 B2 | 4/2004 | Brendzel et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,769,434 B2 | 8/2004 | Liddicoat et al. |
| 6,776,785 B1 | 8/2004 | Yencho |
| 6,786,924 B2 | 9/2004 | Ryan et al. |
| 6,786,925 B2 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,830,585 B1 | 12/2004 | Artof et al. |
| 6,833,924 B2 | 12/2004 | Love et al. |
| 6,837,902 B2 | 1/2005 | Nguyen et al. |
| 6,846,324 B2 | 1/2005 | Stobie |
| 6,846,325 B2 | 1/2005 | Liddicoat |
| 6,872,226 B2 | 3/2005 | Cali et al. |
| 6,893,459 B1 | 5/2005 | Macoviak |
| 6,893,460 B2 | 5/2005 | Spenser et al. |
| 6,896,690 B1 | 5/2005 | Lambrecht et al. |

(56) References Cited

U.S. PATENT DOCUMENTS

| | | |
|---|---|---|
| 6,908,481 B2 | 6/2005 | Cribier |
| 6,911,043 B2 | 6/2005 | Myers et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,929,653 B2 | 8/2005 | Streeter |
| 6,939,365 B1 | 9/2005 | Fogarty |
| 6,945,980 B2 | 9/2005 | Nguyen et al. |
| 6,945,997 B2 | 9/2005 | Huynh et al. |
| 6,960,221 B2 | 11/2005 | Ho et al. |
| 6,974,476 B2 | 12/2005 | McGuckin et al. |
| 7,011,681 B2 | 3/2006 | Vesely |
| 7,025,780 B2 | 4/2006 | Gabbay |
| 7,037,333 B2 | 5/2006 | Myers et al. |
| 7,070,616 B2 | 7/2006 | Majercak et al. |
| 7,083,648 B2 | 8/2006 | Yu |
| 7,097,659 B2 | 8/2006 | Woolfson et al. |
| 7,101,396 B2 | 9/2006 | Artof et al. |
| 7,137,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 | 2/2007 | Shu et al. |
| 7,175,659 B2 | 2/2007 | Hill et al. |
| 7,182,769 B2 * | 2/2007 | Ainsworth et al. ........... 606/142 |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,201,771 B2 | 4/2007 | Lane |
| 7,201,772 B2 | 4/2007 | Schwammenthal et al. |
| 7,214,344 B2 | 5/2007 | Carpentier et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,393,360 B2 | 7/2008 | Spenser et al. |
| 7,422,603 B2 | 9/2008 | Lane |
| 7,445,632 B2 | 11/2008 | McGuckin et al. |
| 7,513,909 B2 | 4/2009 | Lane et al. |
| 7,547,313 B2 | 6/2009 | Gardiner et al. |
| 7,556,647 B2 | 7/2009 | Drews et al. |
| 7,578,843 B2 | 8/2009 | Shu |
| 7,597,711 B2 | 10/2009 | Drews et al. |
| 7,708,775 B2 | 5/2010 | Rowe et al. |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat et al. |
| 7,803,184 B2 | 9/2010 | McGuckin et al. |
| 2001/0007956 A1 | 7/2001 | Letac et al. |
| 2001/0018592 A1 | 8/2001 | Schaller et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077555 A1 | 6/2002 | Schwartz |
| 2002/0077698 A1 | 6/2002 | Peredo |
| 2002/0091441 A1 | 7/2002 | Guzik |
| 2002/0116054 A1 | 8/2002 | Lundell et al. |
| 2002/0123802 A1 | 9/2002 | Snyders |
| 2002/0128684 A1 | 9/2002 | Foerster |
| 2002/0138138 A1 | 9/2002 | Yang |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 | 12/2002 | Klaco |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0045902 A1 | 3/2003 | Weadeock |
| 2003/0055495 A1 | 3/2003 | Pease et al. |
| 2003/0109922 A1 | 6/2003 | Peterson |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 10/2003 | Nguyen et al. |
| 2003/0199963 A1 | 10/2003 | Tower et al. |
| 2003/0199971 A1 | 10/2003 | Tower et al. |
| 2003/0229394 A1 | 12/2003 | Ogle et al. |
| 2003/0236568 A1 | 12/2003 | Hojeibane et al. |
| 2004/0015232 A1 | 1/2004 | Shu |
| 2004/0019374 A1 | 1/2004 | Hojeibane et al. |
| 2004/0024452 A1 | 2/2004 | Kruse et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0044406 A1 | 3/2004 | Woolfson |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0106990 A1 | 6/2004 | Spence et al. |
| 2004/0122514 A1 | 6/2004 | Fogarty |
| 2004/0122516 A1 | 6/2004 | Fogarty |
| 2004/0122526 A1 | 6/2004 | Imran |
| 2004/0167573 A1 | 8/2004 | Williamson, IV et al. |
| 2004/0167620 A1 | 8/2004 | Ortiz et al. |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075730 A1 | 4/2005 | Myers et al. |
| 2005/0080454 A1 | 4/2005 | Drews |

(56) References Cited

U.S. PATENT DOCUMENTS

| | | |
|---|---|---|
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1* | 5/2005 | Realyvasquez et al. ..... 623/2.11 |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137702 A1 | 6/2005 | Haug et al. |
| 2005/0150775 A1 | 7/2005 | Zhang et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0240263 A1 | 10/2005 | Fogarty |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004389 A1 | 1/2006 | Nguyen et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino |
| 2006/0122692 A1 | 6/2006 | Gilad et al. |
| 2006/0135964 A1 | 6/2006 | Vesely |
| 2006/0136052 A1 | 6/2006 | Vesely |
| 2006/0136054 A1 | 6/2006 | Berg et al. |
| 2006/0149360 A1 | 7/2006 | Schwammenthal et al. |
| 2006/0149367 A1 | 7/2006 | Sieracki |
| 2006/0154230 A1 | 7/2006 | Cunanan |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane |
| 2006/0195185 A1 | 8/2006 | Lane |
| 2006/0195186 A1 | 8/2006 | Drews |
| 2006/0207031 A1 | 9/2006 | Cunanan et al. |
| 2006/0229708 A1 | 10/2006 | Powell et al. |
| 2006/0235508 A1 | 10/2006 | Lane |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0276888 A1 | 12/2006 | Lee |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010835 A1 | 1/2007 | Breton et al. |
| 2007/0010876 A1 | 1/2007 | Salahieh et al. |
| 2007/0010877 A1 | 1/2007 | Salahieh et al. |
| 2007/0016285 A1 | 1/2007 | Lane |
| 2007/0016286 A1 | 1/2007 | Herrmann et al. |
| 2007/0016288 A1 | 1/2007 | Gurskis |
| 2007/0027461 A1 | 2/2007 | Gardiner et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0095698 A1 | 5/2007 | Cambron |
| 2007/0100440 A1 | 5/2007 | Figulla et al. |
| 2007/0106313 A1 | 5/2007 | Golden et al. |
| 2007/0129794 A1 | 6/2007 | Realyvasquez |
| 2007/0142848 A1 | 6/2007 | Ainsworth et al. |
| 2007/0142906 A1 | 6/2007 | Figulla et al. |
| 2007/0142907 A1 | 6/2007 | Moaddeb et al. |
| 2007/0150053 A1 | 6/2007 | Gurskis |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0004696 A1 | 1/2008 | Vesely |
| 2008/0033543 A1 | 2/2008 | Gurskis et al. |
| 2008/0071361 A1 | 3/2008 | Tuval et al. |
| 2008/0071369 A1 | 3/2008 | Tuval et al. |
| 2008/0097595 A1 | 4/2008 | Gabbay |
| 2008/0119875 A1 | 5/2008 | Ino et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0112233 A1 | 4/2009 | Xiao |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0210052 A1 | 8/2009 | Forster et al. |
| 2009/0264903 A1 | 10/2009 | Lee et al. |
| 2009/0319038 A1 | 12/2009 | Gurskis et al. |
| 2010/0030244 A1 | 2/2010 | Woolfson et al. |
| 2010/0044410 A1 | 2/2010 | Argentine et al. |
| 2010/0100174 A1 | 4/2010 | Gurskis |
| 2010/0249894 A1 | 9/2010 | Oba et al. |

FOREIGN PATENT DOCUMENTS

| | | |
|---|---|---|
| EP | 0 084 395 | 8/1986 |
| EP | 0 096 721 | 12/1987 |
| EP | 0 125 393 | 12/1987 |
| EP | 0 179 562 | 7/1989 |
| EP | 0 826 340 | 3/1998 |
| EP | 1057460 | 12/2000 |
| EP | 1 088 529 | 4/2001 |
| EP | 1171059 | 1/2002 |
| EP | 971 650 | 1/2005 |
| EP | 171 059 | 2/2005 |
| GB | 1093599 | 12/1967 |
| GB | 1477643 | 6/1977 |
| GB | 2011259 | 7/1979 |
| GB | 2 056 023 | 3/1981 |
| GB | 2 069 843 | 9/1981 |
| GB | 2254254 | 10/1992 |

(56) References Cited

FOREIGN PATENT DOCUMENTS

| | | |
|---|---|---|
| GB | 2 279 134 | 12/1994 |
| SU | 1116573 | 7/1985 |
| WO | 87/05489 | 9/1987 |
| WO | 89/00084 | 2/1989 |
| WO | 91/15167 | 10/1991 |
| WO | 92/01269 | 8/1992 |
| WO | 92/13502 | 8/1992 |
| WO | 92/19184 | 11/1992 |
| WO | 92/19185 | 11/1992 |
| WO | 95/17139 | 6/1995 |
| WO | 95/28899 | 11/1995 |
| WO | 96/40006 | 12/1996 |
| WO | 97/09933 | 3/1997 |
| WO | 97/09944 | 3/1997 |
| WO | 97/27799 | 8/1997 |
| WO | 97/28745 | 8/1997 |
| WO | 97/39688 | 10/1997 |
| WO | 97/41801 | 11/1997 |
| WO | 97/42871 | 11/1997 |
| WO | 98/06329 | 2/1998 |
| WO | 99/11201 | 3/1999 |
| WO | 99/15112 | 4/1999 |
| WO | 99/51169 | 10/1999 |
| WO | 00/32105 | 6/2000 |
| WO | 00/40176 | 7/2000 |
| WO | 00/44311 | 8/2000 |
| WO | 00/56250 | 9/2000 |
| WO | 00/59382 | 10/2000 |
| WO | 00/60995 | 10/2000 |
| WO | 00/64380 | 11/2000 |
| WO | 01/10310 | 2/2001 |
| WO | 01/10312 | 2/2001 |
| WO | 01/49217 | 7/2001 |
| WO | 01/58363 | 8/2001 |
| WO | 01/76510 | 10/2001 |
| WO | 01/82840 | 11/2001 |
| WO | 01/87190 | 11/2001 |
| WO | 03/053289 | 7/2003 |
| WO | 03/063740 | 8/2003 |
| WO | 2004/006810 | 1/2004 |
| WO | 2004/089246 | 10/2004 |
| WO | 2005/004753 | 1/2005 |
| WO | 2005/020842 | 3/2005 |
| WO | 2005/039452 | 5/2005 |
| WO | 2005/072655 | 8/2005 |
| WO | 2006/086135 | 8/2006 |
| WO | 2009/137517 | 11/2009 |

OTHER PUBLICATIONS

Jansen, et al., "Detachable Shape-Memory Sewing Ring for Heart Valves," Artif. Organs.—vol. 16, No. 3, 1992, pp. 294-297, Helmholtz Institute for Biomedical Engineering, Technical University of Aachen, Aachn, Germany.

* cited by examiner

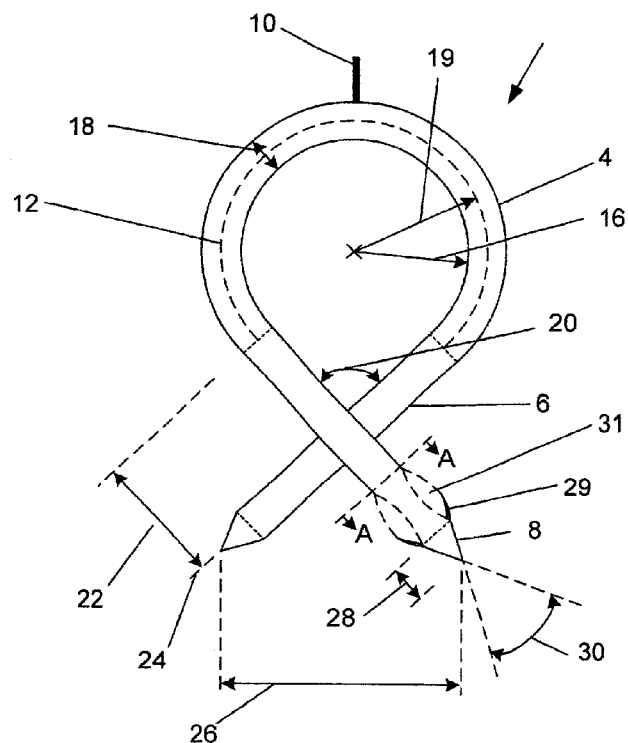
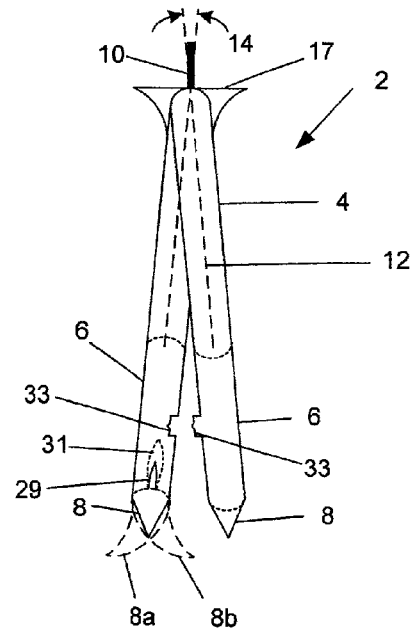
Fig. 1
Fig. 2
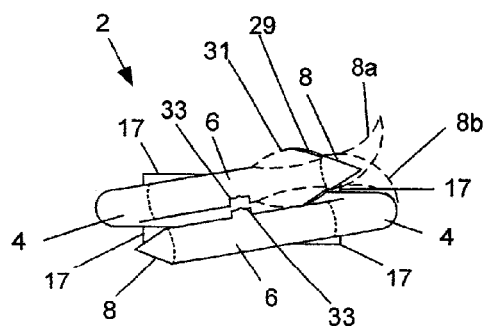
Fig. 3

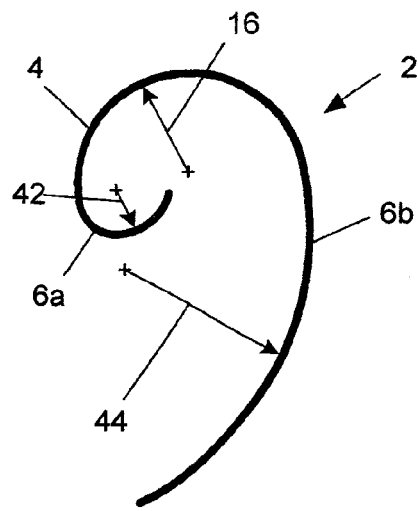
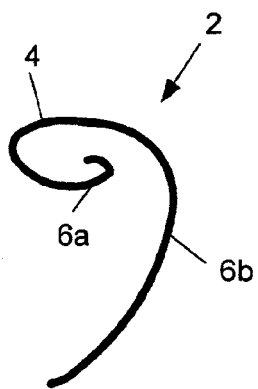
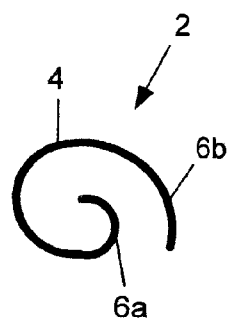
Fig. 15
Fig. 16
Fig. 17
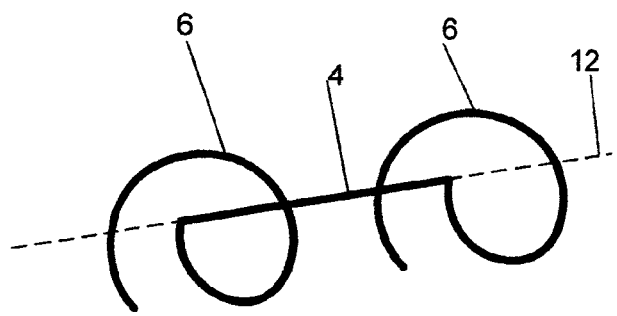
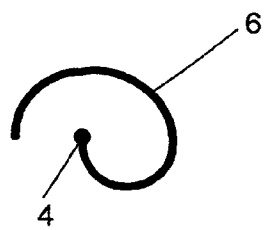
Fig. 18
Fig. 19

ATTACHMENT DEVICE AND METHODS OF USING THE SAME

This application is a continuation of application Ser. No. 10/681,700, filed Oct. 8, 2003, now U.S. Pat. No. 7,556,647.

BACKGROUND OF THE INVENTION

1. Field of the Invention

The present invention relates generally to a device for attaching a first mass to a second mass and methods of making and using the same.

2. Description of the Related Art

Prosthetic heart valves can replace defective human valves in patients. Prosthetic valves commonly include sewing rings, suture cuffs or rings that are attached to and extend around the outer circumference of the prosthetic valve orifice.

In a typical prosthetic valve implantation procedure, the aorta is incised and the defective valve is removed leaving the desired placement site that may include a fibrous tissue layer or annular tissue. Known heart valve replacement techniques include individually passing sutures through the fibrous tissue or desired placement site within the valve annulus to form an array of sutures. Free ends of the sutures are extended out of the thoracic cavity and laid, spaced apart, on the patient's body. The free ends of the sutures are then individually threaded through a flange of the sewing ring. Once all sutures have been run through the sewing ring (typically 12 to 18 sutures), all the sutures are pulled up taught and the prosthetic valve is slid or "parachuted" down into place adjacent the placement site tissue. The prosthetic valve is then secured in place by traditional knot tying with the sutures. This procedure is time consuming as doctors often use three to ten knots per suture.

The sewing ring is often made of a biocompatible fabric through which a needle and suture can pass. The prosthetic valves are typically attached to the sewing rings which are sutured to a biological mass that is left when the surgeon removes the existing valve from the patient's heart. The sutures are tied snugly, thereby securing the sewing ring to the biological mass and, in turn, the prosthetic valve to the heart.

During heart valve replacement procedures, the patient is on heart-lung bypass which reduces the patient's oxygen level and creates non-physiological blood flow dynamics. The longer a patient is on heat-lung bypass, the greater the risk for permanent health damage. Existing suturing techniques extend the duration of bypass and increase the health risks due to heart-lung bypass. Furthermore, the fixturing force created by suturing varies significantly from suture to suture, even for the same medical professional.

In addition, sutures and other attachment devices are used in a variety of medical applications where the use of the device of the present invention would provide an advantage in fixing a first mass to a second mass, where the first mass is a tissue or a device or prosthesis, and the second mass is a tissue or a device or prosthesis. These applications include anchoring a prosthesis such as a synthetic or autologous graft to surrounding tissue or another prosthesis, tissue repair such as in the closure of congenital defects such as septal heart defects, tissue or vessel anastomosis, fixation of tissue with or without a reinforcing mesh for hernia repair, orthopedic anchoring such as in bone fusing or tendon or muscle repair, ophthalmic indications, laparoscopic or endoscopic tissue repair or placement of prostheses, or use by robotic devices for procedures performed remotely.

For these indications and others, there is a need for a fixturing device to minimize the time spent fixturing certain devices or conduits, such as a valve prosthesis and a second mass, a vessel to another vessel or anatomical structure, tissue to tissue, surrounding tissue to a second prosthesis, and the like as described above. Furthermore, there is a need for a device that compliments existing suturing or attachment devices and methods and reduces fixturing times. Also, there is a need for a fixturing device that can be easily removed. There also exist a need to provide a fixturing device that can provide a consistent fixturing force.

BRIEF SUMMARY OF THE INVENTION

A device for connecting a first mass to a second mass is disclosed. The device has a base and a first leg. The base has a base axis, a first end and a second end. The first leg extends from the first end of the base. The device has a first configuration and a second configuration. When the base is rotated with respect to the base axis, the device is in the first configuration. The device can also have a second leg extending from the second end of the base.

Another device for connecting a first mass to a second mass is disclosed. The device has a base, a first leg and a second leg. The base has a base axis, a first end and a second end. The first leg has a first longitudinal axis and a first leg length. The first leg extends from the first end of the base. The second leg has a second longitudinal axis and a second leg length. The second leg extends from the second end of the base. The first leg length is substantially longer than the second leg length.

The device can have a first configuration and a second configuration. When the base is rotated with respect to the base axis, the device is in the first configuration.

Yet another device for connecting a first mass to a second mass is disclosed. The device has a base, a first leg and a second leg. The base is curved. The base has a base diameter, a first end and a second end. The first leg has a first longitudinal axis and a first leg length. The first leg extends from the first end of the base. The second leg has a second longitudinal axis and a second leg length. The second leg extends from the second end of the base. The device has a relaxed configuration. In the relaxed configuration the first leg crosses the second leg at a leg angle. The leg angle is less than 180 degrees.

The leg angle can be less than or equal to 90 degrees. The leg angle can be less than or equal to 60 degrees. The base diameter can be less than or equal to 0.13 inches. The base diameter can be greater than or equal to 0.08 inches.

A method of attaching a first mass to a second mass is disclosed. The method uses an attachment device having a base, a first leg, and a second leg. The base has a first end and a second end. The first leg extends from the first end of the base. The second leg extends from the second end of the base. The attachment device has a first configuration and a second configuration. The method includes holding the attachment device in the first configuration. The method also includes twisting the base of the attachment device to force the attachment device into the second configuration. Further, the method includes inserting the attachment device into the first mass and the second mass. The method also includes releasing the attachment device.

Twisting the base of the attachment device can occur before inserting the attachment device into the first mass. Inserting the attachment device, at least partially, into the first mass can occur before twisting the base of the attachment device.

Another method of attaching a first mass to a second mass is disclosed. The method includes forcibly holding an attachment device in a second configuration. The attachment device has a first configuration and the second configuration. The method also includes inserting the attachment device into the first mass and the second mass. The method also includes releasing the attachment device into the first configuration.

BRIEF DESCRIPTION OF THE DRAWINGS

FIG. 1 is a front view of an embodiment of the attachment device.

FIG. 2 is a side view of an embodiment of the attachment device.

FIG. 3 is a bottom view of an embodiment of the attachment device.

FIGS. 14 and 15 are front views of various embodiments of the attachment device.

FIG. 16 is a front perspective view of an embodiment of the attachment device.

FIG. 17 is a top view of the embodiment of the attachment device shown in FIG. 16.

FIG. 18 is a side perspective view of an embodiment of the attachment device.

FIG. 19 is a side view of the attachment device shown in FIG. 18.

DETAILED DESCRIPTION

Figure 4:
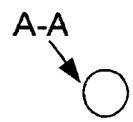
FIGS. 4-10 illustrate embodiments of section A-A of the attachment device.
Figure 5:
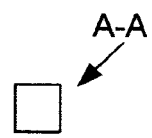
Figure 6:
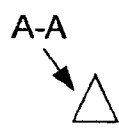
Figure 7:
Figure 8:
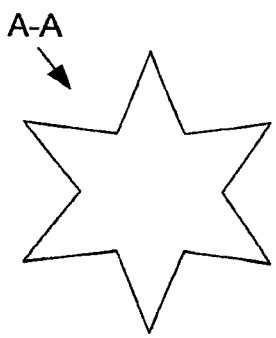

FIGS. 1 through 3 illustrate an attachment device 2. The attachment device 2 can have a base 4, legs 6, and a tip 8 at the end of each leg 6. (Phantom lines delineate the base 4, legs 6 and tips 8.) The base 4, legs 6 and tips 8 can be separate or integral elements. A flag 10 can be attached to, and extend from, the base 4. The base 4 and/or the legs 6 can be straight or curved.

The attachment device 2 can be made from a deformable or elastic material or a combination of materials having resulting deformable or elastic properties. The material can be, for example, stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), polymers such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), extruded collagen, silicone, echogenic, radioactive, radiopaque materials or combinations thereof Examples of radiopaque materials are barium sulfate, titanium, stainless steel, nickel-titanium alloys, tantalum and gold.

Any or all elements of the attachment device 2 can be a matrix for cell ingrowth or used with a fabric, for example a covering (not shown) that acts as a matrix for cell ingrowth. The fabric can be, for example, polyester (e.g., DACRON® from E. I. du Pont de Nemours and Company, Wilmington, Del.), polypropylene, PTFE, ePTFE, nylon, extruded collagen, silicone or combinations thereof.

The attachment device 2 and/or the fabric can be filled and/or coated with an agent delivery matrix known to one having ordinary skill in the art and/or a therapeutic and/or diagnostic agent. These agents can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

A base axis 12 can extend longitudinally through the transverse cross-sectional center of the base 4. As shown in FIG. 2, when viewed from the side, the base axis 12 can form a base plane angle 14 from about 0° to about 30°, for example about 10°. The base 4 can have a base inner radius 16 from about 0.25 mm (0.010 in.) to about 19.1 mm (0.750 in.), for example about 1.91 mm (0.075 in.). The proximal end of the base 4 can be formed into a table 17. The table 17 can be a flat surface that tapers to the base 4.

The base 4 and legs 6 can have a shaft diameter 18 from about 0.03 mm (0.001 in.) to about 6.35 mm (0.250 in.), for example, about 0.51 mm (0.020 in.). The base 4 and legs 6 can have the same or different shaft diameters 18. A base neutral radius 19 can be the base inner radius 16 and half the shaft diameter 18. As shown in FIG. 1, the legs 6 can intersect at a leg angle 20 in or near the plane of the attachment device 2 or in or near the approximate plane of the base 4. An approximate plane is a plane that can be used whether the base 4 does or does not fall on a flat plane. If the base 4 is a straight line or a point, the approximate plane of the base 4 can be calculated using the points of the legs 6 that are nearest the base 4 and out of line with the base 4. The leg angle 20 can be from about 180° to about 10°, more narrowly from about 90° to about 60°, for example about 45° or, for example, about 60°.

The length from an end of the base 4 to a longitudinal leg axis 24 can be a body length 22. The body length 22 can be from about 0.25 mm (0.010 in.) to about 12.7 mm (0.500 in.), for example about 2.913 mm (0.1147 in.). The length between the distal end of one tip 8 and the distal end of the opposite tip 8 can be a tip distance 26. The tip distance 26 can be from about 0.03 mm (0.001 in.) to about 25.4 mm (1.000 in.), more narrowly about 1.3 mm (0.050 in.) to about 3.18 mm (0.125 in.), for example about 2.3 mm (0.090 in.).

The tip 8 can have a tip length 28 from about 0.05 mm (0.002 in.) to about 12.7 mm (0.500 in.), for example about 1.0 mm (0.040 in.). The tip 8 can have a tip angle 30 from about 5° to about 90°, for example about 30°. The tips 8 can be straight, pointed ends, curve out of line (shown by alternative tips 8a and 8b, drawn in phantom lines in FIGS. 2 and 3) from the nearest end of the leg 6, or combinations thereof.

The tips 8 and/or legs 6 can have retention devices 29. The retention devices 29 can be barbs, spikes, hooks, threads, ribs, splines, a roughened surface, a sintered surface, a covered surface (e.g., with DACRON® from E. I. du Pont de Nemours and Company, Wilmington, Del.) or combinations thereof A retention coating 31, for example a biodegradable coating or filler such as gel or gelatin or otherwise removable, can be on and/or around and/or near the retention devices 29. The retention coating 31 (shown in phantom lines) can be configured to render the retention device 29 substantially ineffective until a substantial amount of the retention coating 31 has been biodegraded or otherwise removed.

The legs 6 can have mechanical interfaces 33, for example, a slot, snap, protrusion, latch, catch or combinations thereof The interfaces 33 can be aligned so the interface on one leg 6 meets the interface 33 on the other leg 6 at the point where the legs 6 cross. The interfaces 33 can removably attach to each other.

Figure 9:
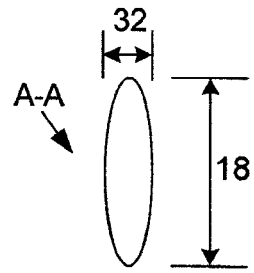

FIGS. 4 through 10 illustrate examples of cross-section A-A of the legs 6 and/or the base 4. The cross-section A-A of the legs 6 can be the same or different as the cross-sections of the base 4. The cross-sections of the base 4 and/or legs 6 can be constant or vary along their respective lengths. FIGS. 4 through 8, respectively, illustrate circular, rectangular (including square), triangular, substantially flat, and star-shaped or irregular cross-sections A-A. FIG. 9 illustrates an oval cross-section A-A. A ratio of the shaft diameter 18 to the length of a minor axis 32 can be from about 1:1 to about 20:1, for example 10:1.

Figure 10:
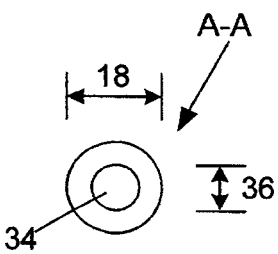

FIG. 10 illustrates a cavity 36 inside the cross-section A-A. The cavity 34 can be hollow or can be filled completely or partially. The cavity 34 can be filled with an agent delivery matrix known to one having ordinary skill in the art and/or a therapeutic and/or diagnostic agent and/or echogenic and/or radioactive and/or radiopaque materials, for example, the agents and/or materials listed supra. The type and amount of filling can vary along the length of the base 4 and/or legs 6. The ratio of the shaft diameter 18 to a cavity diameter 36 can be from about 1:1 to about 50:1, for example, about 2:1.

Figure 11:
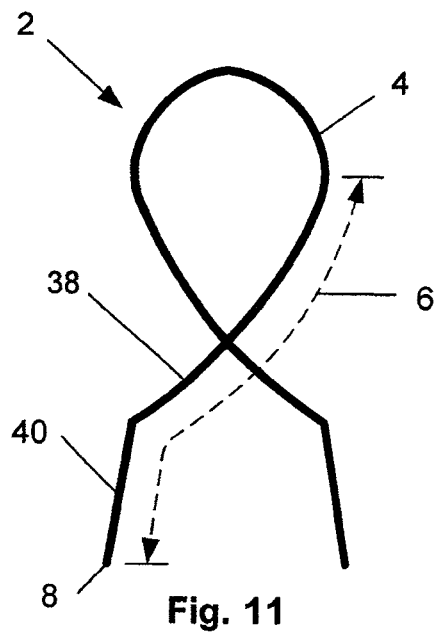
FIG. 11 is a front view of an embodiment of the attachment device.
Figure 12:
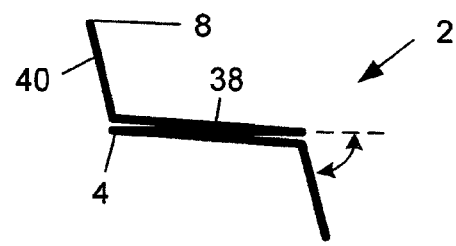
FIGS. 12 and 13 are bottom views of various embodiments of the attachment device shown in FIG. 11.
Figure 13:
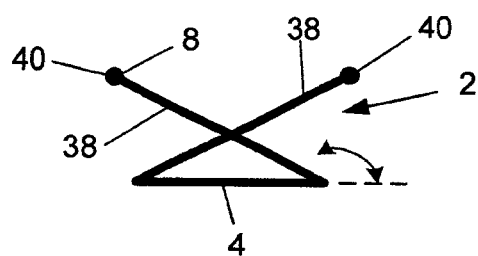

FIG. 11 illustrates an attachment device 2 that can have a leg 6 that can have a first leg segment 38 and a second leg segment 40. The first leg segment 38 can extends from the base 4. The second leg segment 40 can extend on a proximal end from the first leg segment 38. The tip 8 can extend from a distal end of the second leg segment 40. The second leg segment 40 can have a different radius of curvature than the first leg segment 38 and/or form an angle with respect to the first leg segment 40. FIG. 12 illustrates that the second leg segment 40 can form an angle (shown by arrows) with the approximate plane of the base 4. FIG. 13 illustrates that the first leg segment 38 can form an angle (shown by arrows) with the approximate plane of the base 4. The second leg segments 40 can be substantially parallel with the approximate plan of the base 4.

Figure 14:
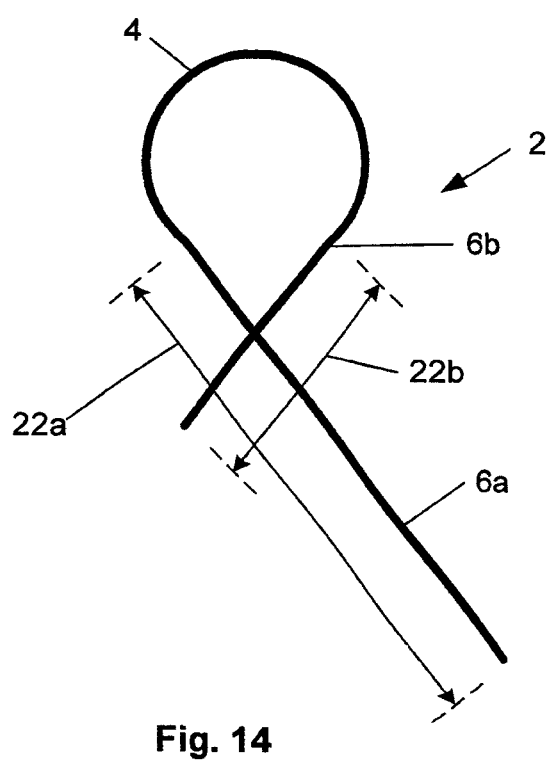

FIG. 14 illustrates an attachment device 2 that can have a first leg 6a that can be substantially longer than a second leg 6b. The ratio of a first leg-tip length 22a to a second leg-tip length 22b can be from about 1:1 to about 10:1, for example, about 3:1.

FIG. 15 illustrates an attachment device that can have a first leg radius 42 and a second leg radius 44. The ratio of the first leg radius 42 to the second leg radius 44 can be from about 1:1 to about 50:1, for example about 10:1.

FIGS. 16 and 17 illustrate an attachment device 2 that can have a "flat top." The approximate plane of the second leg 6b can form an angle, for example about 90°, with the approximate plane of the base 4. When in use, the flat top can further anchor the attachment device 2 against the first mass and/or second mass. FIGS. 18 and 19 illustrate an attachment device 2 that can have arms 6 that can wrap around the base axis 12.

Figure 20:
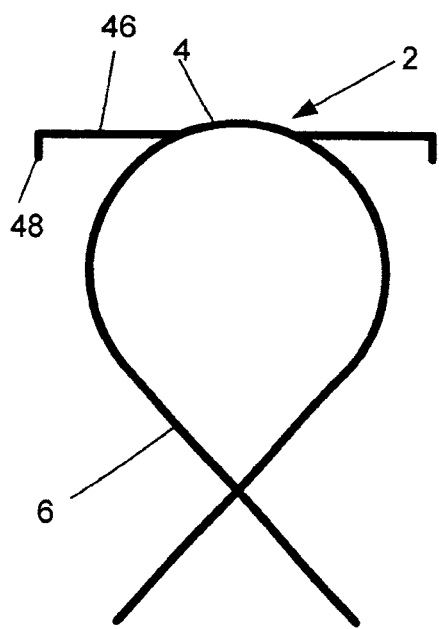
FIGS. 20 and 21 are front views of various embodiments of the attachment device.
Figure 21:
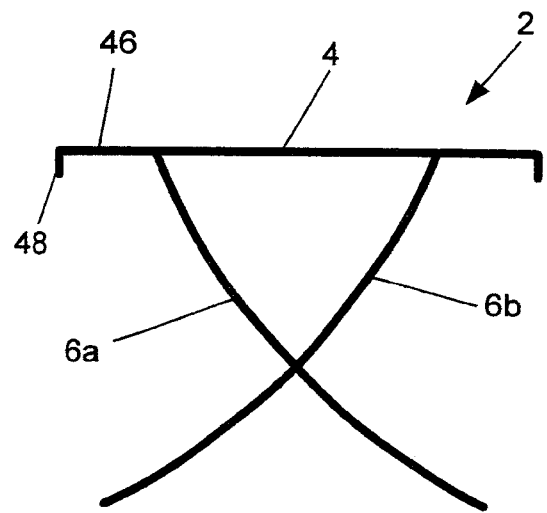

FIG. 20 illustrates an attachment device 2 that can have arms 46 that can extend from the base 4 and/or the legs 6. When deployed, the arms 46 can squeeze tissue between the arms 46 and the legs 6 and/or base 4 for additional retention force. Anchors 48 can extend from the arms 46, for example at the distal ends of the arms 46. The anchors 48 can be, for example, hooks, barbs, spikes, staples or combinations thereof The anchors 48 can extend directly from the base 4 and/or legs 6 with or without arms 46 separately attached to the base 4 and/or legs 6. FIG. 21 illustrates an attachment device 2 that can have a straight base 4 and can have the arms 46 extending from the base 4.

Figure 22:
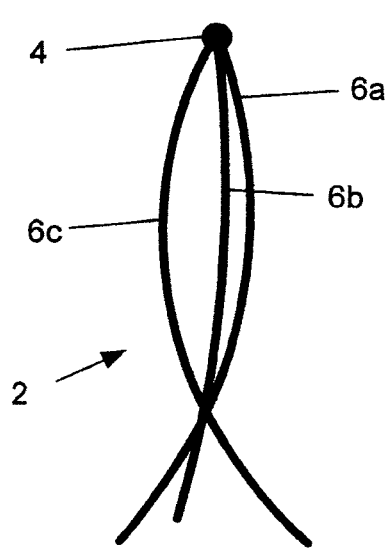
FIG. 22 is a front perspective view of an embodiment of the attachment device.
Figure 23:
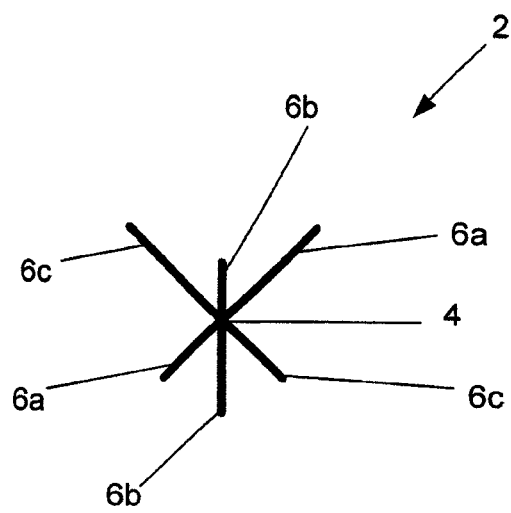
FIG. 23 is a top view of the embodiment of the attachment device shown in FIG. 22.

FIGS. 22 and 23 illustrate an attachment device that can have first, second and third legs 6a, 6b and 6c. The base 4 can be a platform, wireframe, or point attachment which can be spot-welded or brazed, tube crimped or otherwise mechanically connected. The planes of the legs 6a, 6b and 6c can intersect at substantially equal angles, about 120°, or unequal angles.

Figure 24:
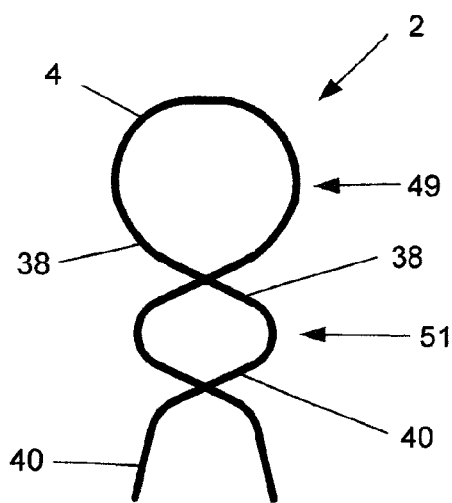
FIG. 24 is a front view of an embodiment of the attachment device.

FIG. 24 illustrates an attachment device that can have a first loop 49 and a second loop 51. The first loop 49 can be formed from the base 4 and a proximal portion of the first leg segments 38. The second loop 51 can be formed from a distal portion of the first leg segments 38 and a proximal portion of the second leg segments 40.

Methods of Making

Figure 25:
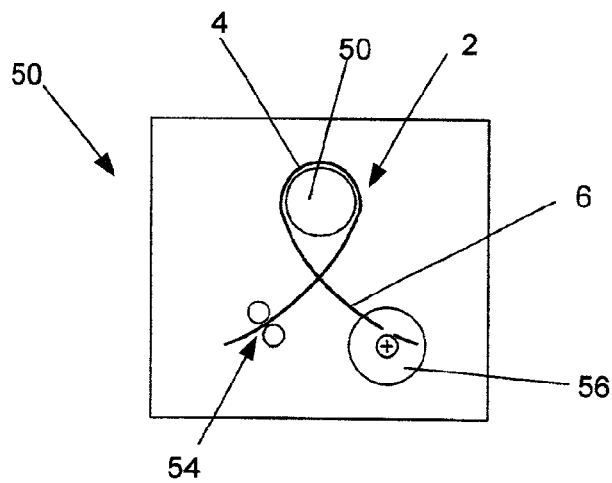
FIG. 25 illustrates an embodiment of a mandrel for manufacturing the attachment device.

FIG. 25 illustrates a mandrel 50 that can be used to form the attachment device 2, for example during heat treatment. The base 4 and/or legs 6 can be held on the mandrel 50 by a single cylinder 52, a formed path 54, a pressure plate 56, for example a washer under a screw or combinations thereof Methods for forming shape memory alloys (e.g., Nitinol) are known to those having ordinary skill in the art. The tips 8 can be formed, for example, by grinding, electropolishing, or precision sharpening (e.g., polishing services from Point Technologies, Inc., Boulder, Colo.) to a satisfactory geometry, including a trocar point, beveled, rounded, tapered, pointed or flattened.

Other methods known to one having ordinary skill in the art can be used to manufacture the attachment device 2 and/or its elements. For example, manufacturing techniques include molding, machining, casting, forming (e.g., pressure forming), crimping, stamping, melting, screwing, gluing, welding, die cutting, laser cutting, electrical discharge machining (EDM), etching or combinations thereof.

Any elements, sub-assemblies, or the attachment device 2 as a whole after final assembly, can be coated by dip-coating or spray-coating methods known to one having ordinary skill in the art, utilizing materials such as PTFE (e.g., TEFLON® from E. I. du Pont de Nemours and Company, Wilmington, Del.), polyester (e.g., DACRON® from E. I. du Pont de Nemours and Company, Wilmington, Del.), gelatin, gel, other polymers or combinations thereof One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating. The coatings can be thrombogenic or anti-thrombogenic.

The attachment device 2, or any element thereof (e.g., the base 4) can be covered with a fabric, for example polyester (e.g., DACRON® from E. I. du Pont de Nemours and Company, Wilmington, Del.), polypropylene, PTFE (e.g., TEFLON® from E. I. du Pont de Nemours and Company, Wilmington, Del.), ePTFE, nylon, extruded collagen, gel, gelatin, silicone or combinations thereof Methods of covering an implantable device with fabric are known to those having ordinary skill in the art, for example, sintering, spray coating, adhesion, loose covering, dipping or combinations thereof.

Methods of Using

The attachment device 2 can have a first configuration (e.g., the configuration shown in FIGS. 26 and 27) and a second configuration (e.g., the configuration shown in FIGS. 1 through 3). The attachment device 2 can have the second configuration when the attachment device is in a relaxed state, with no external forces applied (e.g., prior to insertion or use). The attachment device 2 can have the first configuration when external forces are applied, such as by a delivery tool prior to delivery. When external forces are removed from the attachment device 2, the attachment device 2 can revert from the first configuration to the second configuration.

The attachment device can substantially revert to the second configuration even when some permanent hysteresis deformation occurs and/or when a foreign object (e.g., a first and/or second mass) is obstructing the attachment device 2. When the attachment device 2 has the first configuration, one or both legs 6 can be rotated with respect to the base 4 (e.g., by rotating the base 4 around the base axis 12, one or both legs 6 splay or separate as they are torqued by the twisting or rotating around of the base).

Figure 26:
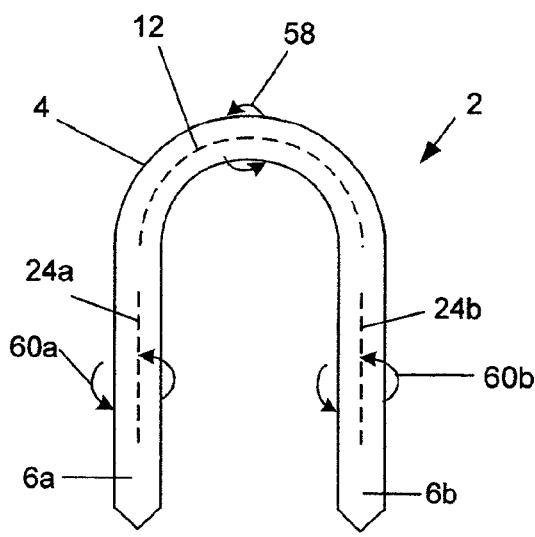
FIGS. 26 and 27 illustrate methods of changing the attachment device from a first configuration to a second configuration.

FIG. 26 illustrates a method of forcing the attachment device to have the first configuration. The attachment device 2 can be forced to have the first configuration by the application of a base torque, shown by arrows 58, applied about the base axis 12. The base torque can be directly applied to the base 4. The base torque indirectly becomes, or can be applied as, a leg torque, as shown by arrows 60*a* and 60*b*, to the legs 6*a* and/or 6*b* about the leg axes 24*a* and 24*b*. If approximately two times the base neutral radius 19 is less than the tip distance 26, the legs 6 will splay outward when entering the first mass 68. If approximately two times the base neutral radius 19 is greater than or equal to the tip distance 26, the legs 6 will splay inward or stay vertical when deploying into the first mass 68.

Figure 27:
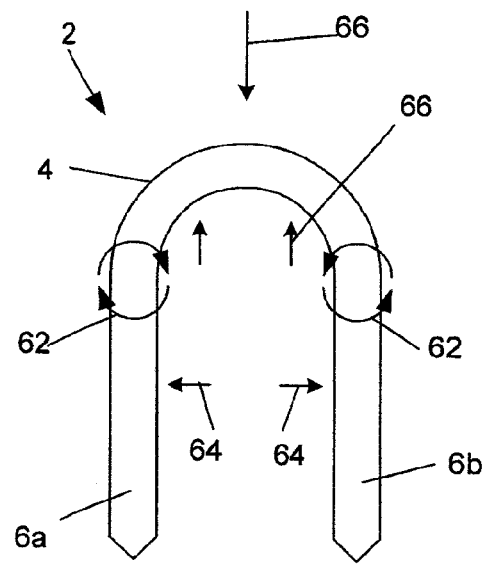

FIG. 27 illustrates a method of forcing the attachment device to have the first configuration. The attachment device 2 can be forced to have the first configuration by the application of a pivot torque, shown by arrows 62, applied about the area where the base 4 attaches to the legs 6, so that the legs 6 are forced to pivot radially outward from each other. The pivot torque can be applied by applying outward translational forces, as shown by arrows 64, to one or both legs 6. The pivot torque can be applied by applying translational forces to the base 4, as shown by arrows 66.

Figure 28:
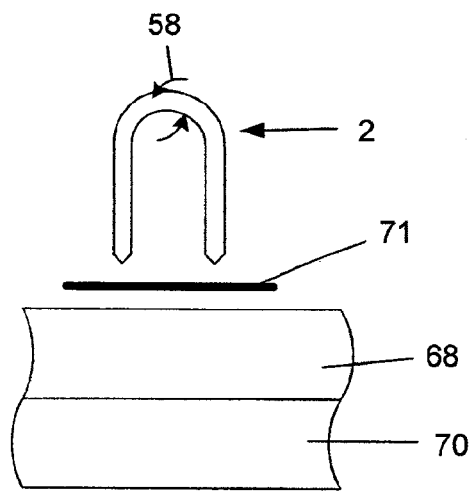
FIGS. 28-30 are cross-sections illustrating an embodiment of a method of using the attachment device.
Figure 29:
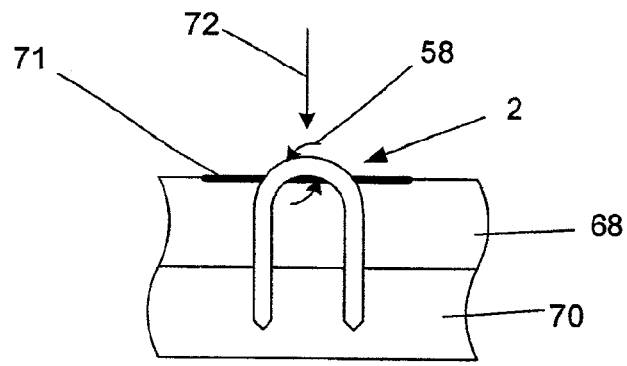
Figure 30:
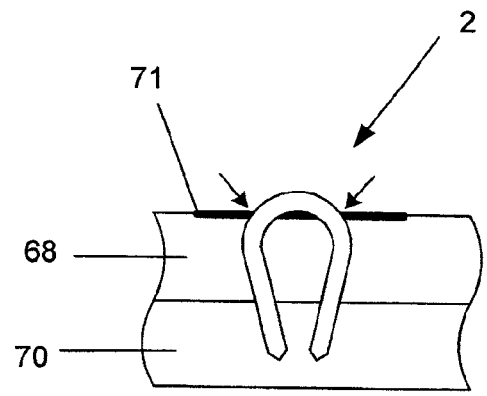

As illustrated in FIGS. 28 through 30, the attachment device 2 can be deployed to attach a first mass 68 to a second mass 70. The first mass 68 and/or the second mass 70 can be a prosthesis and/or a tissue, or both tissue or both prostheses. The prosthesis can be, for example, cardiac leads, markers, stents, grafts, stent-grafts, heart valves, annuloplasty rings, autografts, allografts, xenografts or any assemblies thereof or combination thereof The tissue can be, for example, vessels, valves, organs (e.g., intestine, heart, skin, liver, kidney, urethra, bone mass, tendon, nerve, muscle), calcified soft tissue or any combination thereof.

Heart valve assemblies disclosed by Griffin et al. in U.S. Pat. No. 6,241,765, by Lane in U.S. Pat. No. 6,371,983 and by Ritz in U.S. Pat. No. 5,976,183, both of which are hereby incorporated in their entireties, can be placed with the use of the device of the present invention. Other heart valve assemblies that can be used include, for example, the Advantage Bileaflet heart valve, Parallel valve, Freestyle stentless aortic valve, Hancock Porcine heart valve, Hancock apical left ventricular connector model 174A, Hancock valved conduit models 100, 105, 150, Hall Medtronic heart valve, Hall Medtronic valved conduit, MOSAIC® heart valve and Intact porcine tissue valve (by Medtronic, Inc. Minneapolis, Minn.); Angelini Lamina-flo valve (by Cardio Carbon Company, Ltd., England); Bjork-Shiley single-disk, monostrut and caged-disk valves (Shiley, Inc., now-defunct, previously of CA); Wada-Cutter valve and Chitra Cooley-Cutter valve (by Cutter Biomedical Corp., San Diego, Calif.); Angioflex trileaflet polyurethane valve (by Abiomed, Inc., Danvers, Mass.); ATS AP Series heart valve and ATS Standard heart valve (by ATS Medical, Inc., Minneapolis, Minn.); ANNULOFLO® annuloplasty ring, ANNUFLEX® annuloplasty ring, CARBSEAL® valved conduit, ORBIS® Universal aortic and mitral valve, pediatric/small adult valve, R series valve, SUMIT® mitral valve, TOP HAT® aortic valve, OPTIFORM® mitral valve, MITROFLOW SYNERGY® PC stented aortic pericardial bioprosthesis and the SYNERGY® ST stented aortic and mitral porcine bioprosthesis (by Carbo-Medics, Inc., Austin, Tex.); ON-X® prosthetic heart valve (by MCRI®, LLC, Austin, Tex.); Starr-Edwards SILAS- TIC® ball valve, Starr-Edwards 1000, Starr-Edwards 1200, Starr-Edwards 1260, Starr-Edwards 2400, Starr-Edwards 6300, Starr-Edwards 6500, Starr-Edwards 6520, Carpentier-Edwards porcine tissue valve, Carpentier-Edwards pericardial prosthesis, Carpentier-Edwards supra-annular valve, Carpentier-Edwards annuloplasty rings, Duromedics valve and PERIMOUNT® heart valve (by Edwards Lifesciences Corp., Irvine, Calif.); Cross-Jones Lenticular disc valve (by Pemco, Inc.); Tissuemed stented porcine valve (by Tissuemed, Ltd., Leeds, England); Tekna valve (by Baxter Healthcare, Corp., Deerfield, Ill.); Komp-01 mitral retainer ring (by Jyros Medical Ltd., London, England); SJM® Masters Series mechanical heart valve, SJM® Masters Series aortic valved graft prosthesis, ST. JUDE MEDICAL® mechanical heart valves, ST. JUDE MEDICAL® mechanical heart valve Hemodynamic Plus (HP) series, SJM REGENT® valve, TORONTO SPV® (Stentless Porcine Valve) valve, SJM BIOCOR® valve and SJM EPIC® valve (St. Jude Medical, Inc., St. Paul, Minn.); Sorin Bicarbon, Sorin Carbocast, Sorin Carboseal Conduit, Sorin Pericarbon and Sorin Pericarbon Stentless (by Snia S.p.A., Italy). The attachment devices of the present invention may be deployed to implant these various devices in the supra-annular position, or infrannular, depending on the geometry and preferred placement of a particular device. Similarly, it may be advantageous to use the attachment devices 2 of the present invention to secure a sewing ring, or first prosthesis by placing them horizontally or vertically within or around the annulus of such ring, prior to placing a second prosthesis including a valve structure, as provided in U.S. application Ser. No. 10/646,639 filed, 22 Aug. 2003, hereby incorporated by reference in its entirety.

FIG. 28 illustrates that the attachment device 2 can be held in the first configuration. The attachment device 2 can be fed through a pledget 71 before the attachment device 2 is forced into the first mass 68. The pledget 71 can be a piece of fabric, for example, a fabric listed supra. The pledget 71 can be loaded onto the attachment device 2 before use. FIG. 29 illustrates that the attachment device 2 can be forced, as shown by arrow 72, into and through the first mass 68 and part of the second mass 70. FIG. 30 illustrates that the attachment device 2 can be released from having the first configuration. The attachment device 2 can revert to having substantially the second configuration. A pinching force, shown by arrows, can be applied to the attachment device 2 to encourage additional reversion of the attachment device 2 to having the second configuration. The attachment device 2 shown in FIG. 24 can be deployed in the same manner as described supra, except that the attachment device 2 shown in FIG. 24 can be rotated sufficiently to straighten the first and second loops, before or during deployment.

The attachment device 2 can be removed and redeployed at any stage of deployment supra, for example, if the surgeon is unsatisfied with the position of the attachment device 2, or if the prosthesis need replacing or "redoing" at a point in the future. If the attachment device 2 has a retention device 29, when the retention coating 31 sufficiently biodegrades or is otherwise removed, the retention devices 29 will become exposed and can substantially prevent the removal of the attachment device 2 from the deployment site. Removal may still be achieved however, by apply sufficient force (by a tool or other device) to overcome the strength of the secondary retention element.

Figure 31:
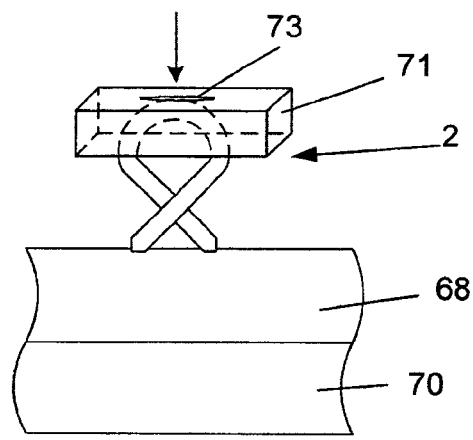
FIGS. 31-33 are cross-sections illustrating an embodiment of a method of using the attachment device with the pledget shown in full perspective for FIGS. 31 and 32.
Figure 32:
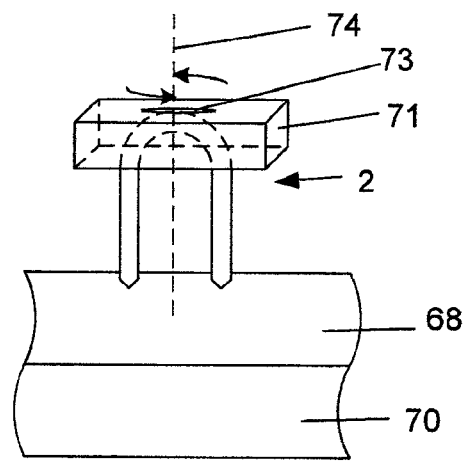
Figure 33:
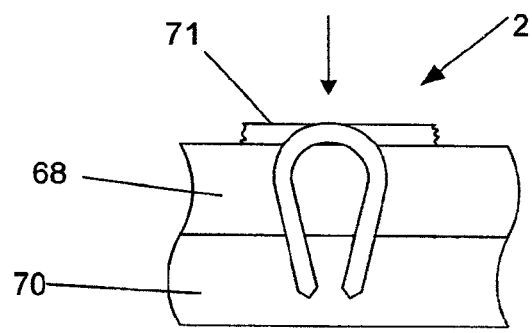

FIGS. 31 though 33 illustrate a method of deploying the attachment device 2 to attach a first mass 68 to a second mass 70. The pledget 71 can be fed over the attachment device 2 before use. The pledget 2 can be formed as a rectangular container with an access opening 73, for example a slit, hole, or aperture, to allow access to the base 4 of the attachment device 2. The attachment device 2 can have the second configuration. The attachment device 2 can be forced, as shown by arrow, so the tips 8 engage the first mass 68. FIG. 32 illustrates that, with the tips 8 held by the first mass 68, a longitudinal torque, shown by arrows, applied to the attachment device 2 about a longitudinal axis 74 can then force the attachment device 2 into the first configuration. As illustrated by FIG. 33, the attachment device 2 can be forced, shown by arrow, through the first mass 68 and part of the second mass 70. The longitudinal torque (not shown in FIG. 33) can be removed during deployment or after the attachment device 2 is completely deployed into the first and second masses 68 and 70. The pledget 71 can be crushed during deployment.

Figures 34, 35:
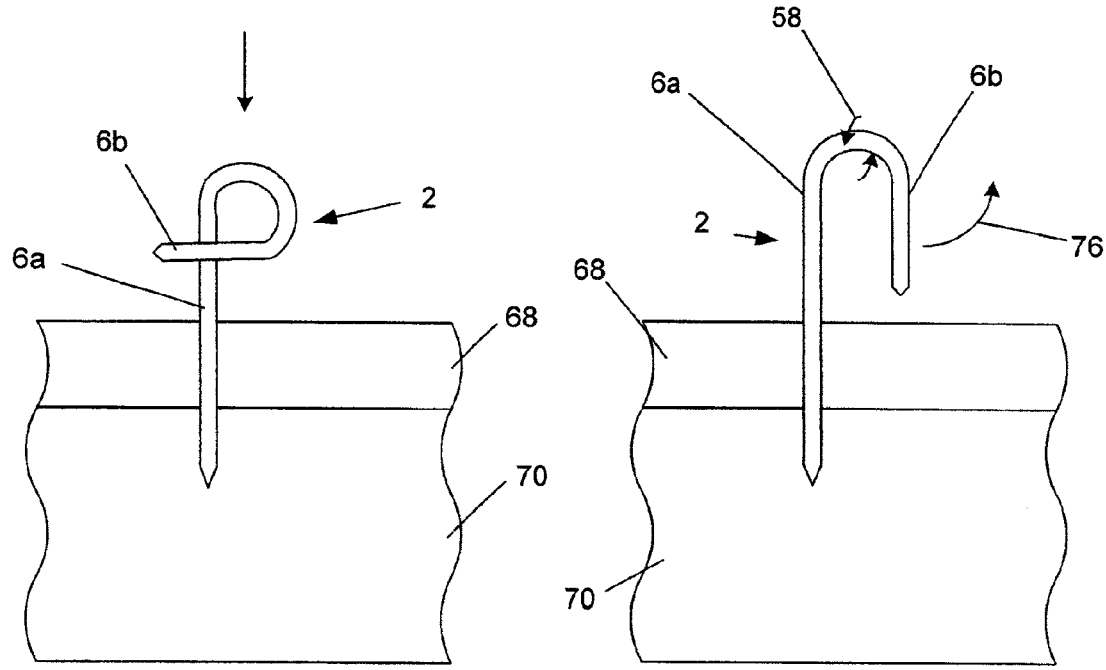
FIGS. 34-36 are cross-sections illustrating an embodiment of a method of using the embodiment of the attachment device shown in FIG. 14.
Figure 36:
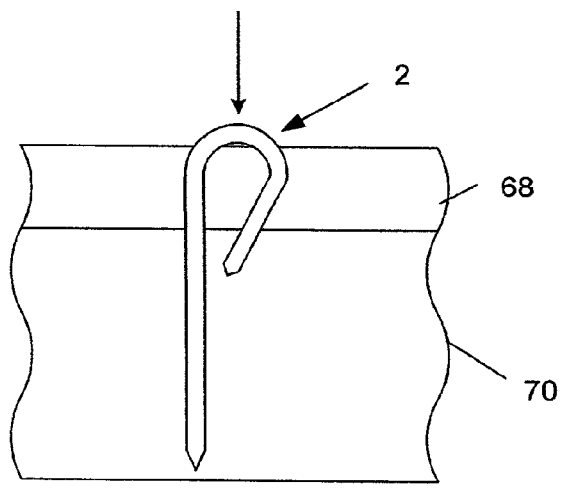

FIGS. 34 through 36 illustrate a method of deploying the attachment device shown in FIG. 14. The first leg 6a can be forced, as shown by arrow, into and through the first mass 68 and part of the second mass 70. The first leg 6a can have a "paddle" (not shown). The paddle can be a flat oval or long rectangular cross-sectional shape on one leg. The paddle can increase resistive force with the first and/or second mass 68 and/or 70 when applying torque to the attachment device 2.

FIG. 35 illustrates that the attachment device 2 can be forced into the first configuration by applying a base torque, shown by arrows 58. The second leg 6b can then rotate outwardly from the attachment device 2, as shown by arrow 76.

FIG. 36 illustrates that the attachment device 2 can be forced, shown by arrow, through the first mass 68 and part of the second mass 70. The base torque (not shown in FIG. 36) can be removed during deployment or after the attachment device 2 is completely deployed into the first and second masses 68 and 70.

Figure 37:
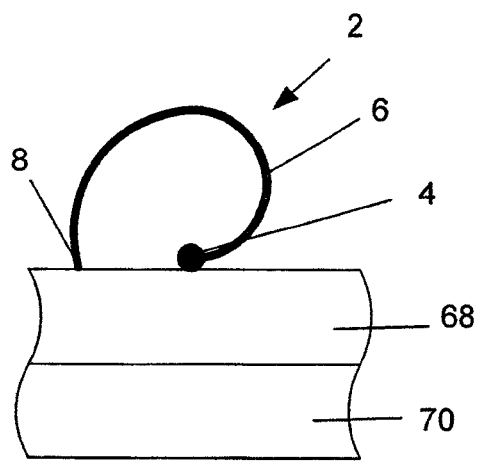
FIGS. 37-39 are cross-sections illustrating an embodiment of a method of using the embodiment of the attachment device shown in FIGS. 18 and 19.
Figure 38:
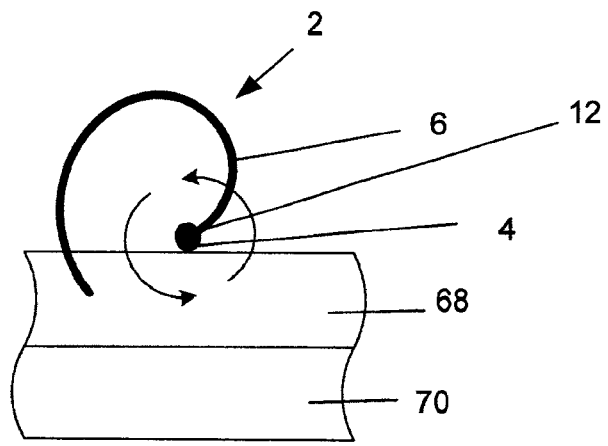
Figure 39:
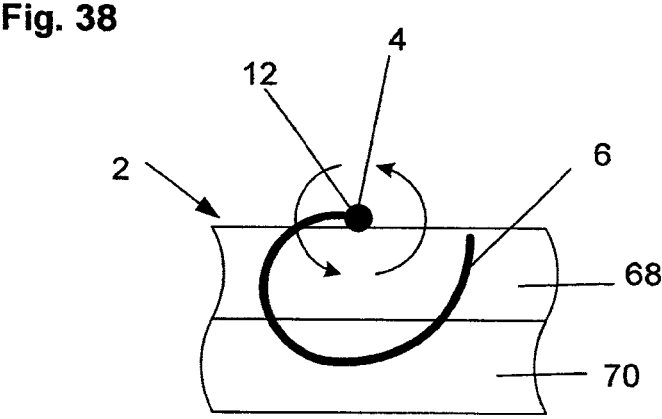

FIGS. 37 through 39 illustrate a method of deploying the attachment device 2 shown in FIGS. 18 and 19. FIG. 37 illustrates that the base 4 and the tips 8 can be placed in contact with or near the first mass 68. FIG. 38 illustrates that the arms 6 can be rotated, as shown by arrows, about the base axis 12. The arms 6 can be rotated to cause the arms 6 to be forced into the first mass 68. FIG. 39 illustrates that the arms 6 can be rotated, as shown by arrows, further about the base axis 12. The arms 6 can be forced into and through the second mass 70. The arms 6 can re-enter the first mass 68.

Figure 40:
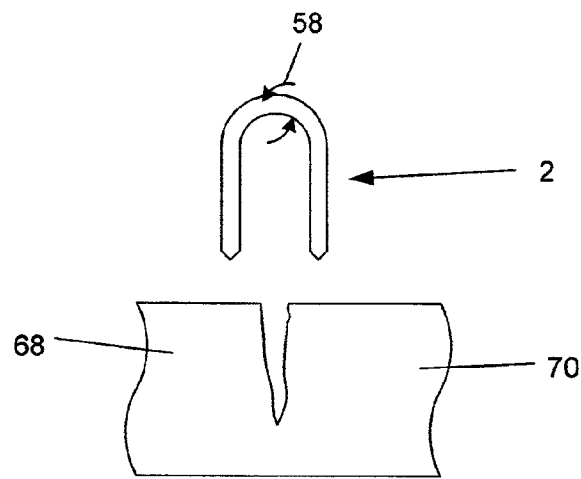
FIGS. 40-42 are cross-sections illustrating an embodiment of a method of using the attachment device.
Figure 41:
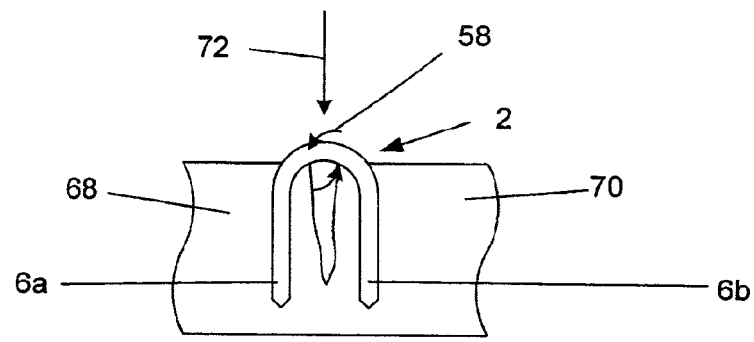
Figure 42:
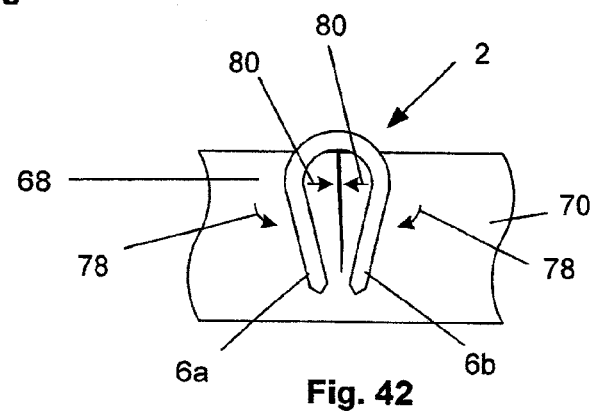

FIGS. 40 through 42 illustrate a method of deploying the attachment device 2 to attach a first mass 68 to a second mass 70. The first mass 68 and the second mass 70 can be two sections of the same object, such as when the attachment device 2 is used to close a wound. FIG. 40 illustrates that the attachment device 2 can be held in the first configuration. FIG. 41 illustrates that the attachment device 2 can be forced, as shown by arrow 72, so that the first leg 6a inserts into the first mass 68 and that the second leg 6b inserts into the second mass 70. FIG. 42 illustrates that the attachment device 2 can be released from having the first configuration. The attachment device 2 can revert to having substantially the second configuration, causing the legs 6a and 6b to rotate inward, shown by arrows 78, applying force, shown by arrows 80, to the first mass 68 and the second mass 70 such that the first and second masses 68 and 70 move toward each other.

The attachment device 2 can be removed from the second mass 70 and/or the first mass 68, when applicable, by reversing the steps of the deployment methods supra.

Figure 43:
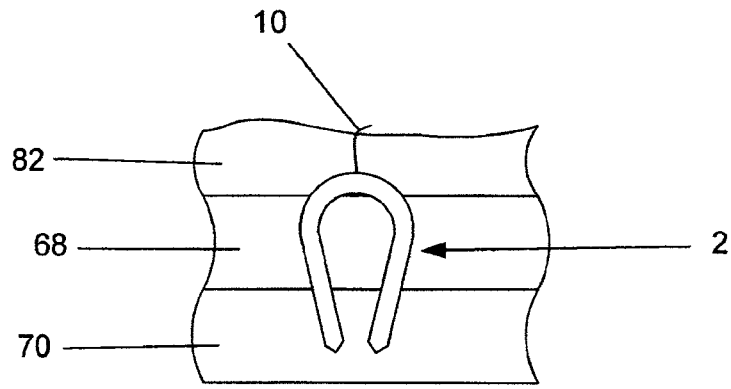
FIG. 43 is a cross-section illustrating a method of using the flag.

FIG. 43 illustrates that, during use, the attachment device 2 can be covered by new tissue growth 82. The flag 10 can extend outside of the new tissue growth 82 (as shown) or be located just below the surface but palpable. The flag 10 can act as a marker, palpable or visible by direct vision or imaging modalities known in the art (e.g., x-ray, magnetic resonance imaging (MRI), ultrasound, computed tomography (CT), echocardiogram) for example to locate the attachment device 2 in case of removal of the attachment device 2. The flag 10 can be made of, for example, suture material (e.g., Nylon, polyglycolic acid, polyester such as DACRON® from E. I. du Pont de Nemours and Company, Wilmington, Del., metals such as those used in the other elements of the attachment device 2, other polymers or combinations thereof). The base 4 can also serve this function (e.g., of a marker) in some applications.

Figure 44:
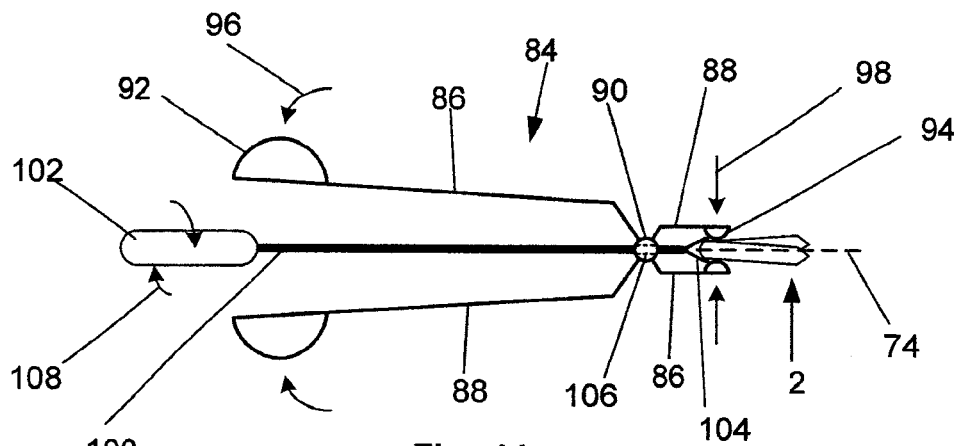
FIG. 44 illustrates an embodiment of the tool for deploying the attachment device.

FIG. 44 illustrates a tool 84 for deploying the attachment device 2. The tool 84 can have a first lever 86 and a second lever 88. The first lever 86 can be rotatably attached to the second lever 88 at a pivot 90. The first and second levers 86 and 88 can have a handle 92 at each lever's first end and a pad 94 at each lever's second end. The pads 94 can be used to hold the attachment device 2. When a force is applied to the handles 92, shown by arrows 96, the force is transmitted, shown by arrows 98, to the pads 94.

A driver shaft 100 can have a driver handle 102 at a first end and grips 104 at a second end. The pivot 90 can have a longitudinal channel 106. The driver shaft 100 can pass through the longitudinal channel 106 and/or be rotatably mounted to a case (not shown) fixed to a lever 86 or 88. The grips 104 can be releasably attached to the attachment device 2. The attachment device 2 can be rotated about the longitudinal axis 2 by releasing the pads 94 and rotating, as shown by arrows 108, the driver handle.

Figure 45:
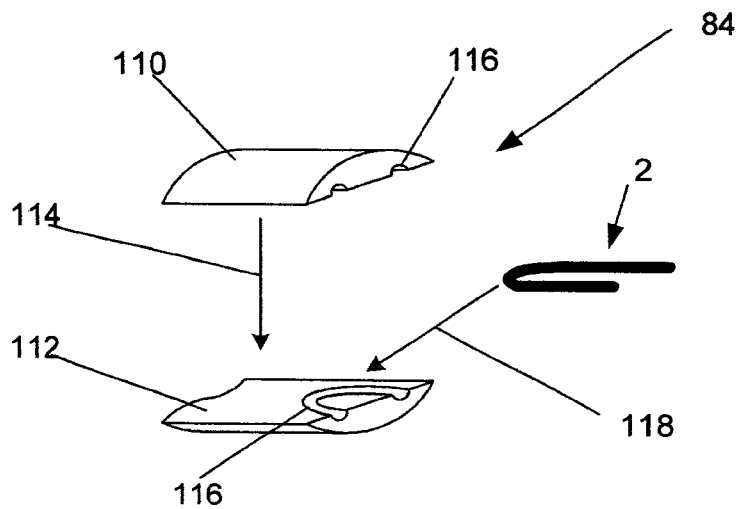
FIG. 45 illustrates the end of a tool for deploying the attachment device.

FIG. 45 shows the end of a tool 84 for deploying the attachment device 2 before the attachment device 2 has been loaded into the tool 84. The tool 84 can have a top part 110 and a bottom part 112. The top part 110 can be removably attached to the bottom part, as shown by arrow 114.

The top part 110 and/or the bottom part 112 can have grooves 116 sized to fit the base 4 and a portion of one or more legs 6 when the attachment device 2 has the first configuration. The attachment device 2 can be forced to have the first configuration and be loaded into the tool 84, as shown by arrow 118. The top part 110 can be attached to the bottom part 112 with the attachment device 2 seated (not shown) in the grooves 116.

The attachment device 2 can be placed at a desired deployment site by the tool 84. The device 2 can be deployed from the tool 84 by removing the top part 110 from the bottom part 112, and removing the tool 84 from the deployment site.

Figure 46:
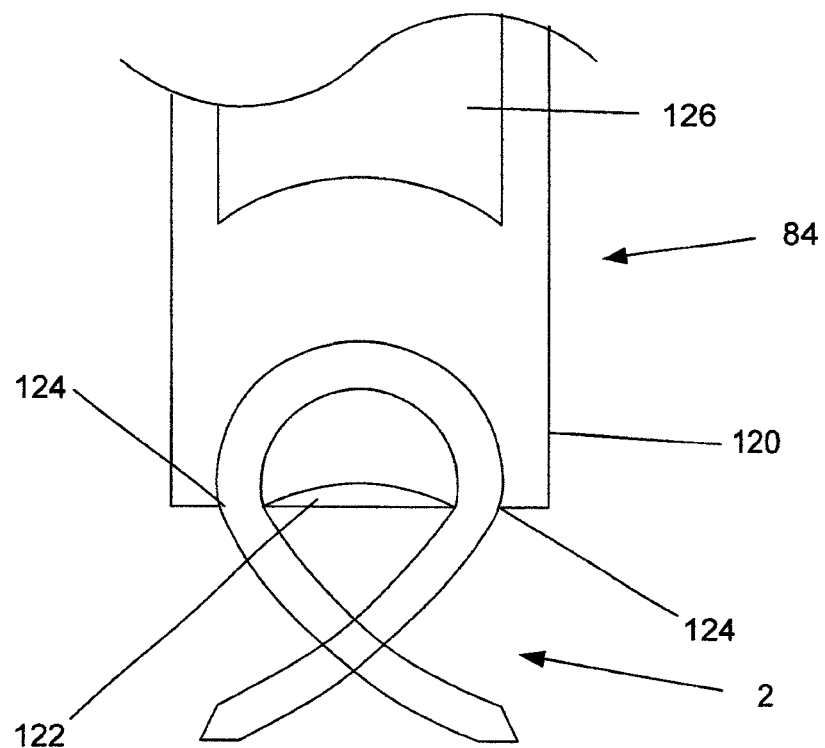
FIGS. 46 and 47 illustrate using the tip of an embodiment of the tool to deploy the attachment device.

FIG. 46 illustrates an end of a tool 84. The tool 84 can have a case 120 with an anvil 122 and leg ports 124. The case 120 can be slidably attached to a slide 126. The attachment device 2 can be loaded around the anvil 122. The legs 6 can protrude from the case 120 through the leg ports 124.

Figure 47:
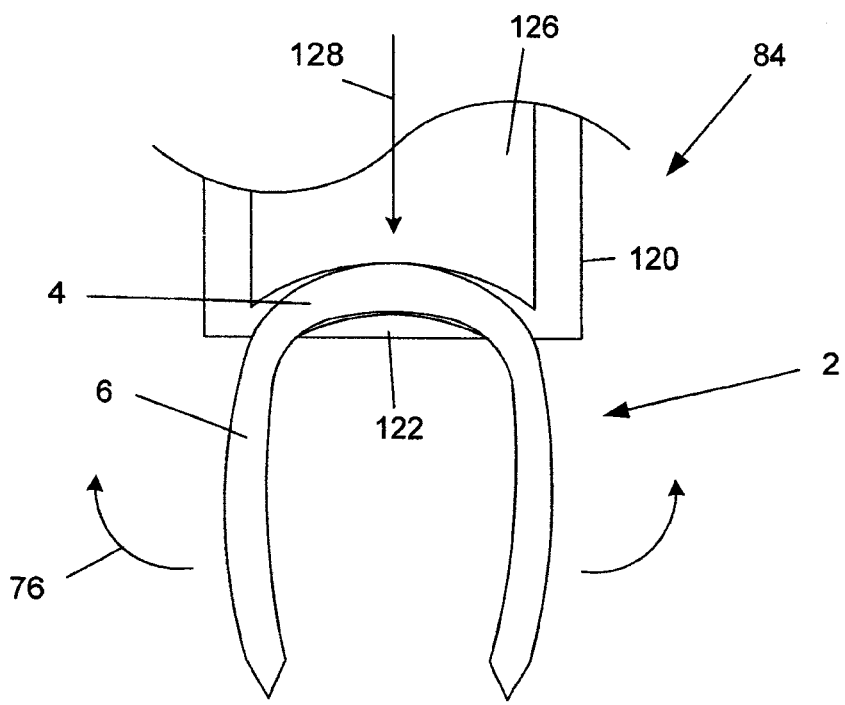

FIG. 47 illustrates a method of using the tool 84 of FIG. 46 to deploy the attachment device 2. The slide 126 can be forced, as shown by arrow 128, toward the anvil 122. The slide 126 can push the base 4 against the anvil 122, causing the legs 6 to rotate outward, as shown by arrows 76. The surface geometry of the anvil 122 and the slider 126 can match the surface geometry of the attachment device 2, when the attachment device is fully strained, as shown in FIG. 39. The attachment device 2 can then be inserted into the desired deployment site (not shown). When the attachment device 2 is in place, the attachment device 2 can be deployed from the tool 84, for example, by sliding the anvil 122 out of the way (perpendicular to the plane of FIG. 47) and forcing the attachment device 2 out the end of the tool 84 with the slide 126.

The ends of the tools 84 shown in FIGS. 45 through 47 can be pivoted to the remainder of the tool 84 by methods known to those having ordinary skill in the art. The pivotable end of the tool 84 can improve access to deployment sites not as easily accessible by a non-articulating tool 84. The tool 84 can be non-articulatable. It would also be possible when access to the site of implantation allows, to employ a tool substantially similar to a needle driver tool known to those skilled in the art.

Additional disclosure is included in U.S. patent application Ser. Nos. 10/327,821 and 10/646,639, filed 20 Dec. 2002 and 22 Aug. 2003, respectively, which are hereby incorporated by reference in their entireties. It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

We claim:

1. A method for attaching a prosthesis to a tissue annulus using an attachment device comprising a base and a pair of legs extending from the base, the attachment device being elastically movable from a relaxed state wherein the legs cross one another and a delivery state wherein the legs extend substantially parallel with one another, the method comprising:
   loading the attachment device into a tool with the attachment device in the relaxed state;
   securing the prosthesis to the tissue annulus using the attachment device while applying a force using the tool to place the attachment device in the delivery state; and
   releasing the attachment device from the tool such that the attachment device returns towards the relaxed state such that the legs cross one another,
   wherein the attachment device is delivered by:
   a) holding the attachment device in the tool in the relaxed state;
   b) applying a force with the tool to force the attachment device to the delivery state;
   c) inserting the legs through the prosthesis into tissue with the attachment device in the delivery state; and
   d) deploying the attachment device from the tool such that the attachment device returns towards the relaxed state.

2. The method of claim 1, wherein the tool comprises an anvil, and step a) comprises loading the attachment device around the anvil in the relaxed state.

3. The method of claim 1, wherein the tool comprises a slide and an anvil for causing the legs of the attachment device to rotate outward to the delivery state during step b).

4. The method of claim 3, wherein step d) comprises sliding the anvil out of the way and forcing the attachment device out the end of the tool with the slide.

5. The method of claim 1, wherein the tool retains the attachment device in the delivery state while the attachment device is inserted through the prosthesis into tissue, whereupon the attachment device is deployed from the tool.

6. A method for attaching an annular prosthesis to a tissue annulus using a plurality of attachment devices, each attachment device comprising a base and a pair of legs extending from the base, the attachment device being elastically movable from a relaxed state wherein the legs cross one another and a delivery state wherein the legs extend substantially parallel with one another, the method comprising:
   loading an attachment device into a tool with the attachment device in the relaxed state;
   securing the annular prosthesis to the tissue annulus using the attachment device while applying a force using the tool to place the attachment device in the delivery state;

releasing the attachment device from the tool such that the attachment device returns towards the relaxed state such that the legs cross one another; and inserting a plurality of additional attachment devices through the prosthesis and into the tissue annulus to further secure the annular prosthesis, wherein each attachment device is delivered by:

a) holding the attachment device in the tool in the relaxed state;

b) applying a force with the tool to force the attachment device to the delivery state;

c) inserting the legs through the annular prosthesis into tissue with the attachment device in the delivery state; and d) deploying the attachment device from the tool such that the attachment device returns towards the relaxed state.

7. The method of claim 6, wherein the annular prosthesis comprises one of a stent, graft, stent-graft, heart valve, annuloplasty ring, autograft, allograft, and a xenograft.

8. The method of claim 6, wherein the annular prosthesis comprises a sewing ring, and wherein the annular prosthesis is attached to the tissue annulus by inserting the attachment devices through the sewing ring.

9. The method of claim 6, wherein the tool comprises an anvil, and step a) comprises loading the attachment device around the anvil in the relaxed state.

10. The method of claim 6, wherein the tool comprises a slide and an anvil for causing the legs of the attachment device to rotate outward to the delivery state during step b).

11. The method of claim 10, wherein step d) comprises sliding the anvil out of the way and forcing the attachment device out the end of the tool with the slide.

12. The method of claim 6, wherein the tool retains the attachment device in the delivery state while the attachment device is inserted through the annular prosthesis into tissue, whereupon the attachment device is deployed from the tool.

13. A method for attaching a heart valve prosthesis to a tissue annulus using attachment devices, each attachment device comprising a base and a pair of legs extending from the base, the attachment devices being elastically movable from a relaxed state wherein the legs cross one another and a delivery state wherein the legs extend substantially parallel with one another, the heart valve prosthesis comprising a first prosthesis comprising a sewing ring and a second prosthesis comprising a valve structure, the method comprising:

securing the first prosthesis to a tissue annulus by inserting the attachment devices through the sewing ring, a tool carrying the attachment devices in the relaxed state, the tool applying a force to place the attachment devices in the delivery state when the attachment devices are inserted through the sewing ring;

releasing the attachment devices from the tool such that the attachment devices return towards the relaxed state such that the legs cross one another; and thereafter placing the second prosthesis, wherein each attachment device is delivered and released by:

a) holding the attachment device in the tool in the relaxed state;

b) applying a force with the tool to force the attachment device to the delivery state;

c) inserting the legs through the first prosthesis into tissue with the attachment device in the delivery state; and d) deploying the attachment device from the tool such that the attachment device returns towards the relaxed state.

* * * * *